(12) United States Patent
Ferre et al.

(10) Patent No.: US 9,177,215 B2
(45) Date of Patent: Nov. 3, 2015

(54) SPARSE REPRESENTATION FOR DYNAMIC SENSOR NETWORKS

(75) Inventors: Wilfredo Ferre, Le Mesnil le Roi (FR); Dimitri Kanevsky, Ossining, NY (US); Tara N. Sainath, New York, NY (US); Marc Yvon, Antony (FR)

(73) Assignee: International Business Machines Corporation, Armonk, NY (US)

( * ) Notice: Subject to any disclaimer, the term of this patent is extended or adjusted under 35 U.S.C. 154(b) by 811 days.

(21) Appl. No.: 13/443,289

(22) Filed: Apr. 10, 2012

(65) Prior Publication Data

US 2013/0268242 A1 Oct. 10, 2013

(51) Int. Cl.
| | | |
|---|---|---|
| G06F 11/00 | (2006.01) | |
| G06K 9/00 | (2006.01) | |
| G01N 33/00 | (2006.01) | |
| G06K 9/62 | (2006.01) | |

(52) U.S. Cl.
CPC ........ *G06K 9/00979* (2013.01); *G01N 33/0075* (2013.01); *G06K 9/6249* (2013.01)

(58) Field of Classification Search
None
See application file for complete search history.

(56) References Cited

U.S. PATENT DOCUMENTS

| 7,392,161 B2 | 6/2008 | Seger | |
|---|---|---|---|
| 2010/0235285 A1* | 9/2010 | Hoffberg | 705/75 |
| 2010/0246920 A1* | 9/2010 | Vaswani | 382/131 |
| 2011/0064302 A1 | 3/2011 | Ma et al. | |
| 2011/0092164 A1 | 4/2011 | Spanhake | |
| 2011/0095908 A1 | 4/2011 | Nadeem et al. | |

FOREIGN PATENT DOCUMENTS

| WO | 2010031128 | 3/2010 |
|---|---|---|
| WO | 2011085368 | 7/2011 |

OTHER PUBLICATIONS

Huang et al., "Sparse Representation for Signal Classification," Neural Information Processing Systems Foundation, Poster Session 7:30 PM Dec. 6, 2006, Vancouver, B.C., Canada.
Donoho et al., "Optimally sparse representation in general (nonorthogonal) dictionaries via (ell)1 minimization," PNAS, Mar. 4, 2003, vol. 100 # 5 pp. 2197-2202.
Elad et al., "A Generalized Uncertainty Principle and Sparse Representation in Pairs of Bases," IEEE Transactions on Information Theory, vol. 48, No. 9, Sep. 2002.
Kanevsky et al., "A-Functions: A Generalization of Extended Baum-Welch Transformations to Convex Optimization," ICASSP 2011, IEEE.
Ramirez et al., "Classification and clustering via dictionary learning with structured incoherence and shared features," 2010 IEEE Computer Society Conference on Computer Vision and Pattern Recognition.

(Continued)

*Primary Examiner* — Aditya Bhat
(74) *Attorney, Agent, or Firm* — Ryan, Mason & Lewis, LLP

(57) ABSTRACT

A method, an apparatus and an article of manufacture for evaluating data from a network of sensors. The method includes analyzing data received from at least one sensor using exemplar-based sparse representation processing to create a sparse representation of the data, determining at least one discrete sparse characteristic of an event in the data received from the at least one sensor based on the sparse representation of the data, and evaluating the at least one discrete sparse characteristic of an event in the data to perform at least one task associated with the representation of the event in the data.

18 Claims, 5 Drawing Sheets

(56) References Cited

OTHER PUBLICATIONS

Carmi et al., "The Use of Isometric Transformations and Bayesian Estimation in Compressive Sensing FMRI Classification." Acoustics Speech and Signal Processing (ICASSP), IEEE International Conference, Mar. 14-19, 2010.

Sainath et al., "Bayesian Compressive Sensing for Phonetic Classification." Acoustics Speech and Signal Processing (ICASSP), IEEE International Conference, Mar. 14-19, 2010.

Candes et al. An Introduction to Compressive Sampling. IEEE Signal Processing Magazine, v. 21, Mar. 2008.

* cited by examiner

(12)  US 9,177,215 B2

SPARSE REPRESENTATION FOR DYNAMIC SENSOR NETWORKS

FIELD OF THE INVENTION

Embodiments of the invention generally relate to information technology, and, more particularly, to data processing.

BACKGROUND

In many situations, data from a sensor network needs to be processed. For example, there can be sensors that are distributed in a city that detect the level of carbon dioxide that is emitted from vehicles. It can be challenging to classify a large amount of data to come to a decision on whether the information from sensors requires some action(s).

Accordingly, there is a need to develop a mathematical solution in order to address this problem.

SUMMARY

In one aspect of the present invention, techniques for sparse representation for dynamic sensor networks are provided. An exemplary computer-implemented method for evaluating data from a network of sensors can include steps of analyzing data received from at least one sensor using exemplar-based sparse representation processing to create a sparse representation of the data, determining at least one discrete sparse characteristic of an event in the data received from the at least one sensor based on the sparse representation of the data, and evaluating the at least one discrete sparse characteristic of an event in the data to perform at least one task associated with the representation of the event in the data.

Another aspect of the invention or elements thereof can be implemented in the form of an article of manufacture tangibly embodying computer readable instructions which, when implemented, cause a computer to carry out a plurality of method steps, as described herein. Furthermore, another aspect of the invention or elements thereof can be implemented in the form of an apparatus including a memory and at least one processor that is coupled to the memory and operative to perform noted method steps. Yet further, another aspect of the invention or elements thereof can be implemented in the form of means for carrying out the method steps described herein, or elements thereof; the means can include (i) hardware module(s), (ii) software module(s), or (iii) a combination of hardware and software modules; any of (i)-(iii) implement the specific techniques set forth herein, and the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

Figure 1:
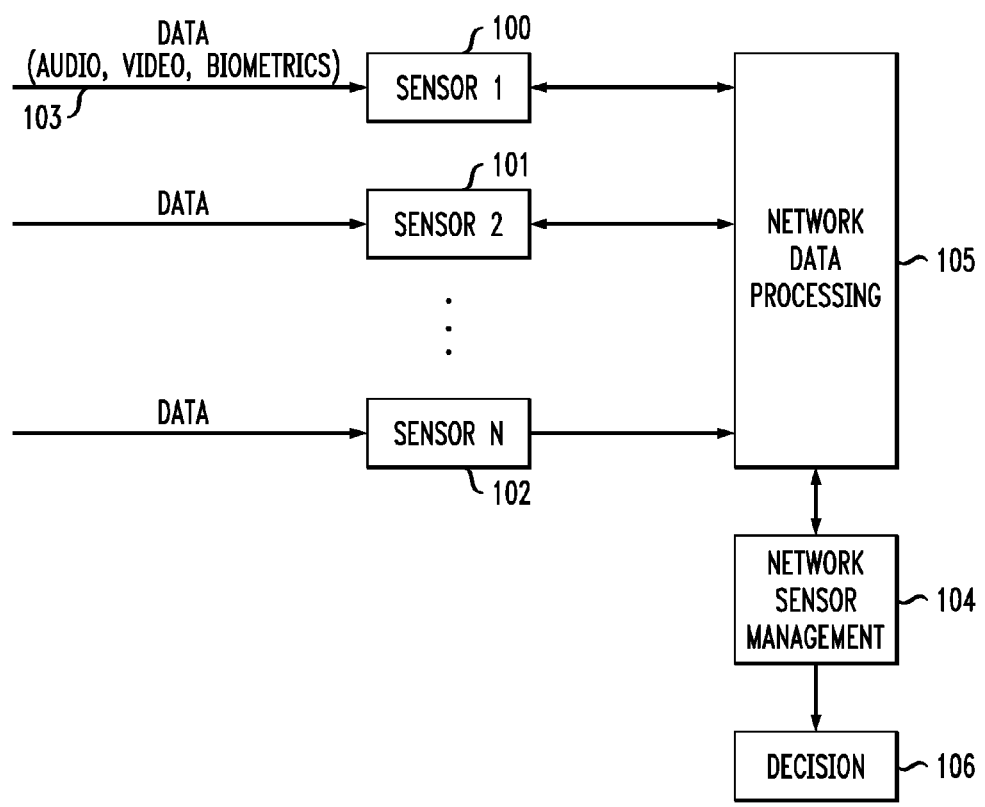
FIG. 1 is a diagram illustrating system components, according to an embodiment of the present invention.

As described herein, an aspect of the present invention includes a sparse solution for a dynamic sensor network. At least one embodiment of the invention includes using an exemplar based method to represent all possible categories of particular situations. After data from sensors is received, a subset of categories of all categories can be chosen that correctly represent the data read from the sensors. In general, there exist many representations that would provide different solutions. In order to ensure that the solution is unique, a matrix that represents all categories can be transformed into a matrix that is the closest to a random matrix. This facilitates receipt of a canonical representation of categories that represent data from sensors.

As detailed herein, aspects of the invention can include unique sparse representation via projection on random matrix and scaling, event detection triggering further measurements, incorporating mobile sensors, restricted isometric property for signal classification, as well as sparse representation for signal classification.

Accordingly, when a sensor value is measured in a given geo-location and interpreted as abnormal or suspicious (for example, a carbon dioxide ($CO_2$) value over a normal threshold), at least one embodiment of the invention includes requesting additional values from other contributors (in proximity to the first sensor). Such additional values can serve multiple purposes. For example, additional values can provide a confidence level (high or lower) to the abnormal measured value, as well as aid in determining if the measured value is indeed an abnormal value or if is there other issues present.

Also, such additional values can define a contaminated (or any other interest) geographical zone to obtain a dynamic network generation of data from multiple data source providers (sensors).

At least one embodiment of the invention includes a sparse representation of a problem of classification of some events in an on-demand network based on some smart participation and collaboration of nearby/surrounding potential participants. By way of illustration, consider the example problem of $CO_2$ concentration. Let $y \in R^m$ be an m-dimensional measurement vector that contains information from some sensors. For example, $y^T = (y_1, y_2, \ldots y_m)$, where $y_i$ contains $CO_2$ levels taken from m sensors in different locations at different times and at different weather conditions (rain, wind, snow, etc.). Assume that a decision is desired as to what class of events the event belongs to in order to perform some action(s) based on the characterization of events. Example characteristics can include a low $CO_2$ level, a strong wind, heavy rain, a high $CO_2$ level, a sensor is in a fast-moving car, a sensor is worn by a walking person, etc.

Additionally, assume that actions can include examples such as more measurements are needed, inform the authorities regarding a high $CO_2$ level, create a zone, etc. Assume also the presence of a database D with m-dimensional vector sensor measurements that were taken in the past and were labeled with characteristics as noted above. Using distance metrics (for example, Euclidean, or based on k-nearest neighbor (kNN) trees), a small amount of m-dimensional vectors can be selected, $h_i$, i=1, 2 ... n that are closest to the test data y. Matrix H is obtained by concatenating vectors $h_i$. Each of columns hi in H is labeled with some characteristic(s), and the objective is a sparse solution $\beta$ for the problem:

$$y = H\beta \qquad (1)$$

$$H = \begin{bmatrix} x_{0.1} & x_{0.2} & x_{1.1} & x_{2.1} \\ 0.2 & 0.3 & 0.7 & 0.1 \\ 0.5 & 0.6 & 0.1 & 0.1 \\ c=0 & c=0 & c=1 & c=2 \end{bmatrix}$$

In at least one embodiment of the invention, the sparse solution can be found using the techniques detailed above in Equation (1). The sparse solution for (1) indicates that most of the entries in $\beta$ are zeroes. The entries that are non-zero in $\beta$ correspond to some significant characteristics for the data y. Assume, for example, that only three entries in $\beta$ are non-zeroes that correspond to columns with characteristics: "low $CO_2$ level," "strong wind," and "heavy rain." Accordingly, at least one embodiment of the invention includes an action module that uses grammar to derive actions from a set of characteristics. The possible action can be expanded to a zone and more measurements can be taken. By way of example, low $CO_2$ during rain and wind conditions may indicate that a significant amount of $CO_2$ dissipated.

At least one embodiment of the invention includes facilitating a decision on a course of action based on information that comes from numerous sensors. This information can be characterized but discrete characteristics describing an outcome from still be obtained from sensors. Accordingly, at least one embodiment of the invention includes requiring that a minimal number of characteristics are produced that adequately describe sensor flow information. By way of example, a determination as to the adequacy of the characteristics can be based on studies and/or experimentation with sensor data. Also, for example, experts can use various statistical and knowledge representation tools to perform such tasks.

There still may be a minimal number of characteristics obtained, and such a minimal set may not be unique. There can be several different sets of minimal characteristics describing the same events, which can make deriving an algorithm for mapping sets of characteristics into required actions challenging. Accordingly, to ensure that a number of subsets of minimal characteristics that describes a flow of information with high probability are substantial, at least one embodiment of the invention carries out the following techniques.

When a sensitivity matrix H is generated from a set of past measurements, entries are chosen that are projections from H to random matrices that were generated using random sampling from a set of vectors that are distributed according to Gaussian distributions. This guarantees that a set of minimal characteristics discovered via solving a corresponding compressive sensing (CS) equation is unique with high probability. More precisely, this algorithm can be described as follows.

Assume that it is desired to have some uniqueness imposed on a solution associated with Equation (1). Let $\tilde{H} \in R^n$ include entries that are samples according $N(0,1/m)$. Let $P: R^{mn} \to R^{mn}$ be an invertible map that minimizes $\|PH - \tilde{H}\|$. Then, a sparse $\beta$ is defined from the problem:

$$Py = \tilde{H}\beta \qquad (2)$$

Because $\tilde{H}$ obeys restricted isometric property (RIP) with overwhelming probability, it has a unique sparse solution.

This scheme can be extended to a dynamic situations when each measurement y and $h_i$ are a set of vectors taken during some time interval. Specifically, solving Equation (1) for several time points in time intervals will produce a time series of characteristics. Accordingly, in at least one embodiment of the invention, an action module can additionally require analysis of this time series of characteristics. The analysis can include items such as, for example, periodicity, pick, convergence, etc.

In at least one embodiment of the invention, an additional way to process vectors from time intervals is to average them. Periodicity can indicate, by way of example that high CO2 each morning and evening indicate that there are traffic increases that lead to higher CO2 levels at those times. Pick can indicate that there is an extraordinary event (for example, a fire). Convergence can indicate that events and conditions are stabilizing.

Accordingly, an aspect of the invention includes providing a sparse solution for representing and activating potential sensors that is extensible. For example, sensors can be added to be participants in the dynamic network, characteristics or events can be added to the model. As such, selecting contributors (sources of data) can be done at a given time with unique sparse capabilities applied to sensor data characteristics along with spatial and time dimensions.

FIG. 1 is a diagram illustrating system components, according to an embodiment of the present invention. By way of illustration, FIG. 1 depicts sensors 100, 101 and 102, which receive data 103 that can include, for example, audio, video and biometrics. As also depicted in FIG. 1, network sensor management module 104 controls the sensors and provides information to a network data processing module 105 and a decision module 106. The network sensor management module 104 is described in more detail in connection with FIG. 2. Network data processing module 105 receives data from network sensor management module 104 and processes the data. Further, the decision maker module 106 is described in more detail in connection with FIG. 3.

Figure 2:
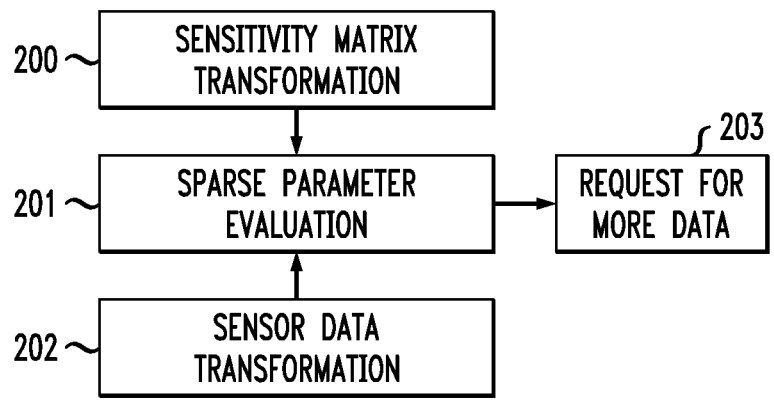
FIG. 2 is a diagram illustrating a network sensor management module, according to an embodiment of the present invention.

FIG. 2 is a diagram illustrating a network sensor management module, according to an embodiment of the present invention. By way of illustration, FIG. 2 depicts a sparse parameter evaluation module 201, which evaluates sparse parameters given information from modules 202 and 200. Accordingly, sensor data transformation module 202 transforms the received sensor data and sensitivity matrix transformation module 200 transforms the sensitivity matrix.

In accordance with at least one embodiment of the invention, the sensitivity matrix can be created from samples of sensor data that are representative of typical characteristics of measurements for given locations. These samples of data are represented as columns in the sensitivity matrix H. Additionally, a technique of transformation of the original sensitivity matrix is described herein in connection with matrix P. A goal of which includes improving properties of the original sensitivity matrix, for example, by requiring that sparse solutions via the transformed matrix are unique with sufficient probability.

Additionally, as described herein, after sparse parameters are evaluated, they are sent to request module 203, which requests more data if needed.

Figure 3:
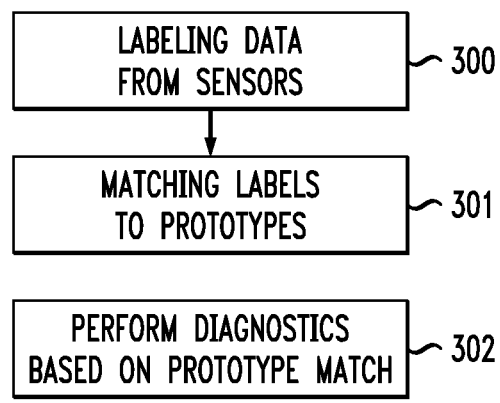
FIG. 3 is a diagram illustrating a decision module, according to an embodiment of the present invention.

FIG. 3 is a diagram illustrating a decision module, according to an embodiment of the present invention. By way of illustration, FIG. 3 depicts data labeling module 300, which labels data received from the sensors. Matching module 301 matches the labels to prototypes, and diagnostics module 302 performs diagnostics based on the prototype match. Prototypes can be generated, for example, by experts on a flow of data obtained in a controllable environment. For instance, a prototype can be some amount of $CO_2$ from certain type of cars that are moving within a certain range of speed that can be observed in a testing laboratory or via controllable testing in an external environment (on streets, etc.).

Figure 4:
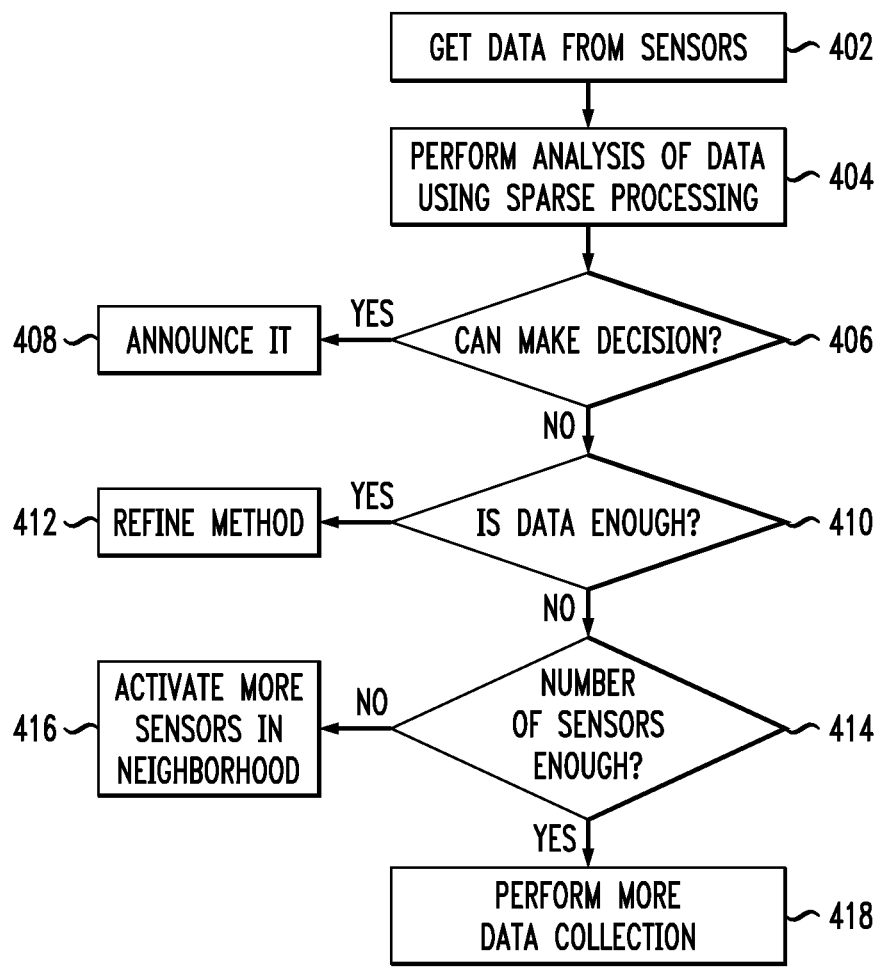
FIG. 4 is a flow diagram illustrating techniques for selectively activating data sensors, according to an embodiment of the present invention.

FIG. 4 is a flow diagram illustrating techniques for selectively activating data sensors, according to an embodiment of the present invention. Step 402 includes obtaining data from various sensors. Step 404 includes performing analysis of the data using sparse processing. Step 406 includes determining whether or not a decision can be made at this point (that is, whether or not the particular collection of data sensors is sufficient for the specific task at hand). If yes (that is, a decision can be made), step 408 includes announcing the decision. If no (that is, a decision cannot be made), step 410 includes determining whether or not the obtained data is sufficient to make a decision.

If yes (that is, the data is sufficient), step 412 includes refining the method. For example, refining can include processing additional data from remote sensors, decreasing the level of sparseness that was chosen for the data analyses, or using a different objective function to obtain scores for parameters. If no (that is, the data is insufficient), step 414 includes determining whether the number of sensors used is sufficient to make a decision. If yes (that is, the number of sensors is sufficient), step 418 includes performing more data collection. If no (that is, the number of sensors is insufficient), step 416 includes activating more sensors in the proximate neighborhood.

Figure 5:
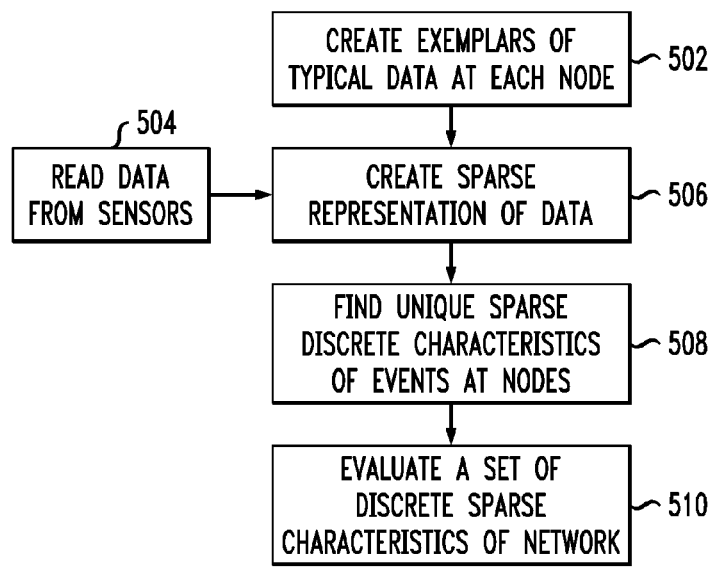
FIG. 5 is a flow diagram illustrating techniques for evaluating sparse characteristics of a network, according to an embodiment of the present invention.

FIG. 5 is a flow diagram illustrating techniques for evaluating sparse characteristics of a network, according to an embodiment of the present invention. Step 502 includes creating exemplars of typical data at each node of a network. Step 504 includes reading data from sensors. Input generated in steps 502 and 504 is used in step 506 to create sparse representation of the data. Additionally, step 508 includes determining unique sparse discrete characteristics of events at the nodes of the network, and step 510 includes evaluating a set of determined discrete sparse characteristics of the network.

Figure 6:
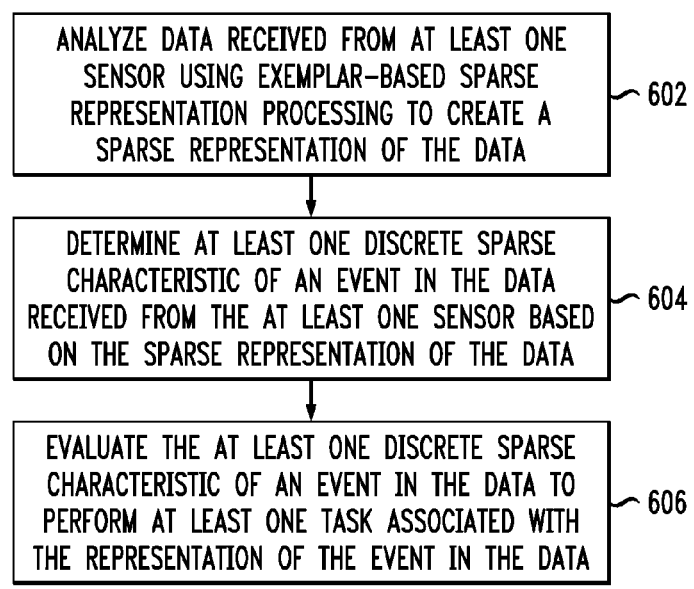
FIG. 6 is a flow diagram illustrating techniques for evaluating data from a network of sensors, according to an embodiment of the invention.

FIG. 6 is a flow diagram illustrating techniques for evaluating data from a network of sensors, according to an embodiment of the present invention. Step 602 includes analyzing data received from at least one sensor using exemplar-based sparse representation processing to create a sparse representation of the data. Using exemplar-based sparse representation processing can include representing multiple categories of possible events. Also, analyzing data received from at least one sensor using exemplar-based sparse representation processing to create a sparse representation of the data can include selecting a subset of at least one category from the multiple categories that represents the data received from at least one sensor.

Selecting a subset of at least one category from the multiple categories that represents the data received from at least one sensor can include transforming a matrix that represents the multiple categories to a matrix or analog thereof (as close as possible, for example) that provides unique sparse representation with sufficient probability. Also, selecting a subset of at least one category from the multiple categories that represents the data received from at least one sensor can include transforming a matrix that represents the multiple categories to a random matrix or analog thereof (as close as possible, for example). Further, at least one embodiment of the invention includes projecting a matrix that is constructed from exemplars onto the random matrix.

Step 604 includes determining at least one discrete sparse characteristic of an event in the data received from the at least one sensor based on the sparse representation of the data. Step 606 includes evaluating the at least one discrete sparse characteristic of an event in the data to perform at least one task associated with the representation of the event in the data. In accordance with at least one embodiment of the invention, examples of tasks related to sensors can include checking that collected data is sufficient for further processing, checking that sparse representation is accurate, unique, minimal, etc., and classification of events (for example, fire, bad design of engines that results in high $CO_2$, etc.).

Evaluating the at least one discrete sparse characteristic of an event in the data to determine accuracy of the representation of the event in the data can further include requesting additional data from at least one additional sensor. Also, at least one embodiment of the invention includes defining a geographical zone of interest to obtain a dynamic network generation of data from multiple sensors.

The techniques depicted in FIG. 6 can additionally include reading data from the at least one sensor, as well as creating at least one exemplar of typical data at each sensor in the network. Further, at least one embodiment of the invention includes labeling the data received from the at least one sensor, and matching the labeled data to an exemplar.

The techniques depicted in FIG. 6 can also, as described herein, include providing a system, wherein the system includes distinct software modules, each of the distinct software modules being embodied on a tangible computer-readable recordable storage medium. All the modules (or any subset thereof) can be on the same medium, or each can be on a different medium, for example. The modules can include any or all of the components shown in the figures. In an aspect of the invention, the modules can run, for example on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 6 can be implemented via a computer program product that can include computer useable program code that is stored in a computer readable storage medium in a data processing system, and wherein the computer useable program code was downloaded over a network from a remote data processing system. Also, in an aspect of the invention, the computer program product can include computer useable program code that is stored in a computer readable storage medium in a server data processing system, and wherein the computer useable program code is downloaded over a network to a remote data processing system for use in a computer readable storage medium with the remote system.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in a computer readable medium having computer readable program code embodied thereon.

An aspect of the invention or elements thereof can be implemented in the form of an apparatus including a memory and at least one processor that is coupled to the memory and operative to perform exemplary method steps.

Figure 7:
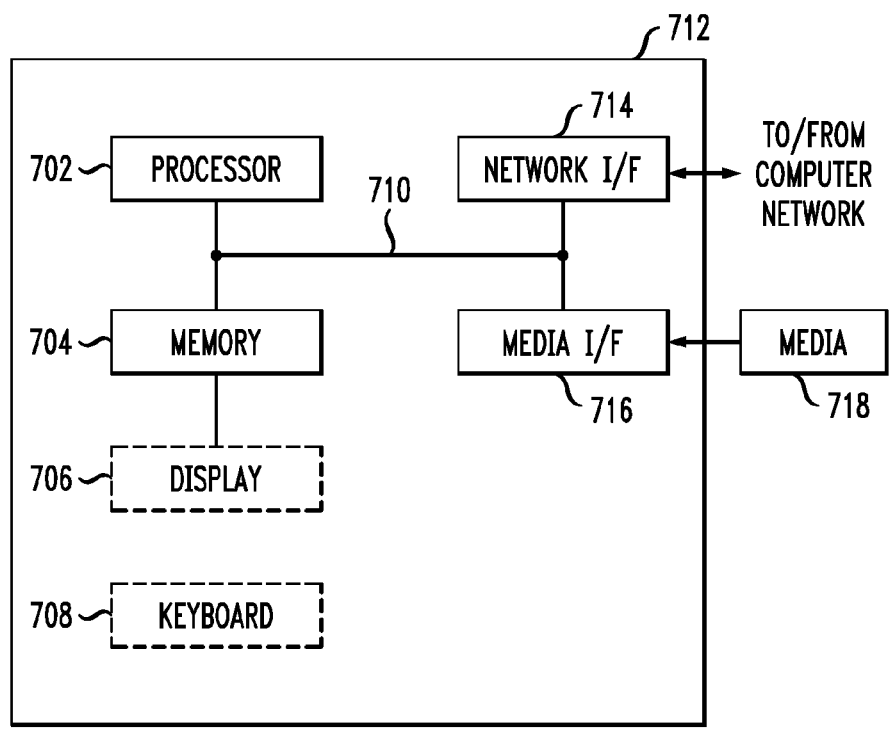
FIG. 7 is a system diagram of an exemplary computer system on which at least one embodiment of the invention can be implemented.

Additionally, an aspect of the present invention can make use of software running on a general purpose computer or workstation. With reference to FIG. 7, such an implementation might employ, for example, a processor 702, a memory 704, and an input/output interface formed, for example, by a display 706 and a keyboard 708. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 702, memory 704, and input/output interface such as display 706 and keyboard 708 can be interconnected, for example, via bus 710 as part of a data processing unit 712. Suitable interconnections, for example via bus 710, can also be provided to a network interface 714, such as a network card, which can be provided to interface with a computer network, and to a media interface 716, such as a diskette or CD-ROM drive, which can be provided to interface with media 718.

Accordingly, computer software including instructions or code for performing the methodologies of the invention, as described herein, may be stored in an associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 702 coupled directly or indirectly to memory elements 704 through a system bus 710. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 708, displays 706, pointing devices, and the like) can be coupled to the system either directly (such as via bus 710) or through intervening I/O controllers (omitted for clarity).

Network adapters such as network interface 714 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 712 as shown in FIG. 7) running a server program. It will be understood that such a physical server may or may not include a display and keyboard.

As noted, aspects of the present invention may take the form of a computer program product embodied in a computer readable medium having computer readable program code embodied thereon. Also, any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of at least one programming language, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. Accordingly, an aspect of the invention includes an article of manufacture tangibly embodying computer readable instructions which, when implemented, cause a computer to carry out a plurality of method steps as described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, component, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 702. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, an appropriately programmed general purpose digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of another feature, integer, step, operation, element, component, and/or group thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

At least one aspect of the present invention may provide a beneficial effect such as, for example, selecting contributors (source of data) at a given time with unique sparse capabilities applied to sensor data characteristics along with spatial and time dimensions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for evaluating data from a network of sensors, wherein the method comprises:

capturing data from multiple physical sensors in the network of sensors, wherein said data comprises carbon dioxide-related data, and wherein said capturing comprises establishing a communicative link between the multiple physical sensors and a network sensor management module executing on a hardware processor of a computing device;

analyzing the data received from the multiple physical sensors using exemplar-based sparse representation processing representing multiple categories of possible events to create a sparse representation of the data, wherein said analyzing comprises selecting a subset of at least one category from the multiple categories that represents the data received from the multiple physical sensors, and wherein said analyzing is carried out by a network data processing module, executing on the hardware processor of the computing device and communicatively linked to the network sensor management module;

determining at least one discrete sparse characteristic of an event in the data received from the multiple physical sensors based on the sparse representation of the data;

classifying the data into one of multiple event classifications based on evaluation of the at least one discrete sparse characteristic of an event in the data; and performing at least one task associated with the representation of the event in the data based on said classifying;

wherein (i) said determining, (ii) said classifying, and (iii) said performing are carried out by a decision maker module, executing on the hardware processor of the computing device and communicatively linked to the network sensor management module and the network data processing module.

2. The method of claim 1, further comprising:
creating at least one exemplar of typical data at each sensor in the network.

3. The method of claim 1, wherein selecting a subset of at least one category from the multiple categories that represents the data received from the multiple physical sensors comprises transforming a matrix that represents the multiple categories to a matrix or analog thereof that provides unique sparse representation with sufficient probability.

4. The method of claim 1, wherein selecting a subset of at least one category from the multiple categories that represents the data received from the multiple physical sensors comprises transforming a matrix that represents the multiple categories to a random matrix or analog thereof.

5. The method of claim 4, further comprising:
projecting a matrix that is constructed from exemplars onto the random matrix.

6. The method of claim 1, wherein evaluating the at least one discrete sparse characteristic of an event in the data to perform at least one task associated with the representation of the event in the data further comprises requesting additional data from at least one additional sensor.

7. The method or claim 6, further comprising:
defining a geographical zone of interest to obtain a dynamic network generation of data from multiple sensors.

8. The method of claim 1, further comprising:
labeling the data received from the multiple physical sensors; and
matching the labeled data to an exemplar.

9. An article of manufacture comprising a non-transitory computer readable storage medium having computer readable instructions tangibly embodied thereon which, when implemented, cause a computer to carry out a plurality of method steps comprising:
capturing data from multiple physical sensors in the network of sensors, wherein said data comprises carbon dioxide-related data, and wherein said capturing comprises establishing a communicative link between the multiple physical sensors and a network sensor management module executing on a hardware processor of a computing device;
analyzing the data received from the multiple physical sensors using exemplar-based sparse representation processing representing multiple categories of possible events to create a sparse representation of the data, wherein said analyzing comprises selecting a subset of at least one category from the multiple categories that represents the data received from the multiple physical sensors, and wherein said analyzing is carried out by a network data processing module, executing on the hardware processor of the computing device and communicatively linked to the network sensor management module;

determining at least one discrete sparse characteristic of an event in the data received from the multiple physical sensors based on the sparse representation of the data;

classifying the data into one of multiple event classifications based on evaluation of the at least one discrete sparse characteristic of an event in the data; and performing at least one task associated with the representation of the event in the data based on said classifying;

wherein (i) said determining, (ii) said classifying, and (iii) said performing are carried out by a decision maker module, executing on the hardware processor of the computing device and communicatively linked to the network sensor management module and the network data processing module.

10. The article of manufacture of claim 9, wherein the computer readable instructions which, when implemented, further cause a computer to carry out a method step comprising:
creating at least one exemplar of typical data at each sensor in the network.

11. The article of manufacture of claim 9, wherein evaluating the at least one discrete sparse characteristic of an event in the data to perform at least one task associated with the representation of the event in the data further comprises requesting additional data from at least one additional sensor.

12. The article of manufacture of claim 11, wherein the computer readable instructions which, when implemented, further cause a computer to carry out a method step comprising:
defining a geographical zone of interest to obtain a dynamic network generation of data from multiple sensors.

13. The article of manufacture of claim 9, wherein the computer readable instructions which, when implemented, further cause a computer to carry out a method step comprising:
labeling the data received from the multiple physical sensors; and
matching the labeled data to an exemplar.

14. A system for evaluating data from a network of sensors, comprising:
a memory; and
at least one processor coupled to the memory and operative for:
capturing data from multiple physical sensors in the network of sensors, wherein said data comprises carbon dioxide-related data, and wherein said capturing comprises establishing a communicative link between the multiple physical sensors and a network sensor management module executing on the at least one processor;
analyzing the data received from the multiple physical sensors using exemplar-based sparse representation processing representing multiple categories of possible events to create a sparse representation of the data, wherein said analyzing comprises selecting a subset of at least one category from the multiple categories that represents the data received from the multiple physical sensors, and wherein said analyzing is carried out by a network data processing module, executing on the at least one processor of the computing device and communicatively linked to the network sensor management module;

determining at least one discrete sparse characteristic of an event in the data received from the multiple physical sensors based on the sparse representation of the data;

classifying the data into one of multiple event classifications based on evaluation of the at least one discrete sparse characteristic of an event in the data; and performing at least one task associated with the representation of the event in the data based on said classifying;

wherein (i) said determining, (ii) said classifying, and (iii) said performing are carried out by a decision maker module, executing on the at least one processor of the computing device and communicatively linked to the network sensor management module and the network data processing module.

15. The system of claim 14, wherein the at least one processor coupled to the memory is further operative for:
creating at least one exemplar of typical data at each sensor in the network.

16. The system of claim 14, wherein the at least one processor coupled to the memory operative for evaluating the at least one discrete sparse characteristic of an event in the data to perform at least one task associated with the representation of the event in the data is further operative for requesting additional data from at least one additional sensor.

17. The system of claim 16, wherein the at least one processor coupled to the memory is further operative for:
defining a geographical zone of interest to obtain a dynamic network generation of data from multiple sensors.

18. The system of claim 14, wherein the at least one processor coupled to the memory is further operative for:
labeling the data received from the multiple physical sensors; and
matching the labeled data to an exemplar.

* * * * *